United States Patent
Bergmann et al.

(10) Patent No.: US 6,235,476 B1
(45) Date of Patent: May 22, 2001

(54) PROCESS FOR DETECTING NUCLEIC ACIDS BY MASS DETERMINATION

(75) Inventors: Frank Bergmann, Iffeldorf; Rupert Herrmann, Weilheim; Uwe Kobold, Wielenbach, all of (DE)

(73) Assignee: Dako A/S, Glostrup (DK)

( * ) Notice: Subject to any disclaimer, the term of this patent is extended or adjusted under 35 U.S.C. 154(b) by 0 days.

(21) Appl. No.: 09/242,536
(22) PCT Filed: Aug. 18, 1997
(86) PCT No.: PCT/EP97/04494
§ 371 Date: Mar. 17, 1999
§ 102(e) Date: Mar. 17, 1999
(87) PCT Pub. No.: WO98/07885
PCT Pub. Date: Feb. 26, 1998

(30) Foreign Application Priority Data

Aug. 20, 1996 (DE) ............................................. 196 33 436

(51) Int. Cl.[7] ....................................................... C12Q 1/68
(52) U.S. Cl. .................................................. 435/6; 436/94
(58) Field of Search ................................. 435/6; 436/94; 536/24.31, 24.32

(56) References Cited

U.S. PATENT DOCUMENTS

| 5,453,247 | 9/1995 | Beavis et al. | 422/68.1 |
|---|---|---|---|
| 5,605,798 | * 2/1997 | Koster | 435/6 |
| 5,780,232 | * 1/1999 | Arlinghaus et al. | 435/6 |
| 5,861,250 | * 1/1999 | Stanley et al. | 435/6 |
| 6,043,031 | * 3/2000 | Koster et al. | 435/6 |

FOREIGN PATENT DOCUMENTS

95/15974   6/1995 (WO).
96/29431   9/1996 (WO).

OTHER PUBLICATIONS

Greig et al., Rapid Communications in Mass Spectrometry, vol. 10, 47–50 (1996) "Negative Ionization Micro Electrspray Mass Spectrometry of Oligonucleotides and their Complexes."

Solouki et al., Anal. Chem. 1995, 67, 4139–4144, "Attomole Biomolecule Mass Analysis by Matrix–Assisted Laser Desorption/Ionization Fourier Tranform Ion Cyclotron Resonance."

Griffith et al., J. Am. Chem. Soc., 1995, 117, 831–832, "Single and Bis Peptide Nucleic Acids as Triplexing Agents: Binding and Stoichiometry".

Butler et al., Anal. Chem., 1996, 68, 3283–3287, "Peptide Nucleic Acid Characterization by MALDI–TOF Mass Spectrometry."

Sambrook J. et al., Cold Spring Harbor Laboratory, 1989, 7.58, "Molecular cloning: A laboratory manual".

Tang et al., Rapid Communications in Mass Spectrometry, vol. 8, 727–739 (1994), "Detection of 500–Nucleotide DNA by Laser Desporption Mass Spectrometry".

Wilm et al., Analytical Chemistry, 1996, 68, "Parent Ion Scans of Unseparated Peptide Mixtures".

* cited by examiner

Primary Examiner—Kenneth R. Horlick
(74) Attorney, Agent, or Firm—Arent Fox Kintner Plotkin Kahn PLLC.

(57) ABSTRACT

A method for detecting nucleic acids by binding a probe P to a partial sequence S contained in the nucleic acid to produce a binding product B1, degrading the nucleic acid to produce a binding product B2 containing a partial nucleic acid F of a defined length and detecting the binding product B2 or the partial nucleic acid F a part based on its mass is particularly suitable for the parallel detection of nucleic acid of different sequences.

17 Claims, 3 Drawing Sheets

SEQUENCE LISTING

```
<160> NUMBER OF SEQ ID NOS: 1

<210> SEQ ID NO: 1
<211> LENGTH: 45
<212> TYPE: DNA
<213> ORGANISM: Artificial Sequence
<220> FEATURE:
<223> OTHER INFORMATION: Description of Artificial Sequence:other
      nucleic acid

<400> SEQUENCE: 1
tattaggcca tcgtcttcat ggtccagaac accaacagga agacc                45
```

PROCESS FOR DETECTING NUCLEIC ACIDS BY MASS DETERMINATION

The invention concerns a method for detecting nucleic acids based on their mass and a reagent suitable for carrying out this method.

Nucleic acids are being used more and more in analytics as an indicator for the presence of microorganisms or for the genetic state of an organism. The reason for this is the amount of information which is contained in nucleic acids. The detection of mutations at the nucleic acid level is considered to be useful especially in the field of diagnosing genetic diseases.

In one type of nucleic acid detection the hybridization of labelled probes with the nucleic acids to be detected is evaluated as an indication for the presence of the nucleic acid to be detected. These tests can be carried out heterogeneously as well as homogeneously. In heterogeneous assays, after a sample preparation step the isolated target nucleic acid is usually amplified by a nucleic acid amplification method such as e.g. PCR according to EP-B-0 200 362, it is then immobilized on a solid phase and subsequently detected with an analyte-specific probe that is labelled directly or indirectly with a signal-generating reporter group. Frequently used labels are radioactive or non-radioactive. Enzymes also come into consideration as a label in which the enzyme catalyses a certain detection reaction. In homogeneous assays no binding to a solid phase takes place.

Intercalator compounds are often used for this which undergo a change in a measurable physical variable after intercalation in the double strand composed of analyte nucleic acid and probe such as an increase in their fluorescence (Nucleic Acids Research, 1995, 23 (5), 753–760) or a change in their fluorescence polarization. In homogeneous assays according to WO 92/02638 a probe which contains a fluorescence label as well as a fluorescence quencher is used. During the assay the label is cleaved from the quencher and the fluorescence activity is detected. The said heterogeneous and homogeneous assays require the use of chemically complicated, specially labelled probes. These are, on the one hand, complicated to prepare and, on the other hand, for each label it must be determined whether it adversely affects the hybridization efficiency.

A method for sequencing DNA is described in U.S. Pat. No. 5,453,247. In this method a set of nucleic acid fragments is produced based on the DNA whose nucleotide sequence is to be determined, wherein each set ends with one or more of the four nucleobases. All possible fragments (single stranded) of the region that is to be sequenced have to be generated. The individual fragments each differ by one nucleotide. The mass of each of these fragments is determined by mass spectrometry.

A method for the detection of nucleic acids is described in WO 95/15974 in which a labelled nucleic acid analogue probe is contacted with the nucleic acid to be detected, the nucleic acid is degraded down to the region protected by the probe and the presence of the complex is detected with the aid of the probe label.

J. Am. Chem. Soc. 1995, 117, 831–832 and Rapid Communications in Mass Spectrometry, 10 47–50 (1996) describe mass spectra of complexes composed of a peptide nucleic acid (PNA) and an oligonucleotide in which the oligonucleotide was prepared synthetically and is the same size as or larger than the region which binds to the PNA molecule by base-base interactions.

The object of the present invention was to provide a nucleic acid detection method which does not require labelled probes and which allows a parallel determination of different nucleic acids.

Therefore a subject matter of the invention is a method for detecting nucleic acids by binding a probe P to a partial sequence S contained in the nucleic acid to produce a binding product B1, degrading the nucleic acid to produce a binding product B2 containing a partial nucleic acid of a defined length and detecting the binding product B2 or a part thereof based on its mass.

A nucleic acid within the sense of the invention means all nucleic acids such as RNA and DNA known to a person skilled in the art. Double-stranded as well as single-stranded nucleic acids can be detected. In the preferred case that the probe P has strand-displacing properties, it is possible to use double-stranded nucleic acids in the method according to the invention without prior denaturation.

The nucleic acids to be detected can be degraded in a defined manner. The source of the nucleic acids to be detected is unimportant. However, a sample containing the nucleic acid to be detected is preferably subjected to a pre-treatment so that the nucleic acids are present in solution and are accessible to dissolve probes. Especially when detecting nucleic acids from cells or organisms, it has proven to be advantageous to destroy the nucleic acids by partial or complete degradation of the cell walls surrounding the nucleic acids. A variety of methods are known for this to a person skilled in the art such as digestion with the aid of proteases in the presence of detergents or/and chaotropic salts. Although it is in principle possible and even preferable within the sense of the invention to already detect nucleic acids from lysed crude samples prepared in this manner, it is, however, also possible to firstly purify the nucleic acids of interfering sample components e.g. by binding the nucleic acids to solid phases e.g. to glass-like surfaces in the presence of chaotropic salts and removing non-bound sample components. The nucleic acids bound to the solid phase can be subsequently removed again from the surface for example by low salt buffers (e.g. according to WO 95/01359).

The invention also sets no limits with regard to the function of the nucleic acids. The nucleic acids can be genomic i.e. long nucleic acids, but also nucleic acids which have already been partially reduced in size, or transcripts. The nucleic acids are particularly preferably products of a nucleic acid amplification such as the polymerase chain reaction (PCR) according to EP-B-0 201 184. In the PCR nucleic acids to be detected in the sample are amplified by contacting the sample with two primers one of which is complementary to a first strand and the other is complementary to its opposite strand on the nucleic acid to be detected. The primers are selected such that the product of an extension of the one primer can serve in turn as a template to extend the other primer using the nucleic acid to be detected as the template. The extension is carried out by a DNA polymerase using monodeoxy-ribonucleoside triphosphates. The extension products are separated between the individual extension steps from the respective templates by denaturation e.g. by a heat step. Such an amplification enables the specific amplification of a certain part of a nucleic acid even in the presence of other nucleic acids. Therefore the nucleic acids to be detected are not only naturally occurring nucleic acids but also amplified or/and modified nucleic acids.

A characteristic of the nucleic acid to be detected is the presence of a partial sequence S in the nucleic acid. This partial sequence is composed of a sequence of nucleic acid bases of a certain and previously known sequence. The partial sequence is preferably larger than 5 nucleotides, preferably between 6 and 100 nucleotides, particularly preferably between 10 and 30 nucleotides long. The partial sequence is preferably on a region of the nucleic acid that is accessible to the probe. It contains the sequence information which is intended to be the basis for the detection e.g. a sequence within which a certain mutation is presumed to occur or which is characteristic for a certain organism. This mutation can be one or several point mutations, one or several deletions, one or several insertions or polymorphisms. Mutations are particularly preferred which are an indicator for an infection by an organism, a genetic disease or a predisposition for such a disease. Examples of such mutations are deviations in the P53 gene. An example of the detection of an infection is the detection of hepatitis C virus based on the presence of HCV-RNA as described in EP-A-0 318 216. In this case a cDNA is for example produced from the HCV-RNA and this is amplified with the aid of PCR in the desired partial region e.g. within the non-coding region.

The method according to the invention is particularly suitable for the parallel determination of nucleic acids of different sequence, origin or/and function. This is then based on different partial sequences of these nucleic acids. The partial sequences S can be of the same length or of different length but they preferably have different base sequences.

Within the sense of the invention a probe P is understood as a molecule which can bind to the partial sequence S of the nucleic acid to be detected. The binding occurs via base-base interactions, in particular Watson-Crick or/and Hoogsten base pairing. The sequence of the probe P is preferably selected such that it is completely i.e. 100% complementary in the region of the partial sequence S to this partial sequence. However, this requirement is only absolutely necessary when nucleic acids are present in the sample which contain a partial sequence that is very similar to the partial sequence S but which should not be detected i.e. in the preferred case of using a probe that is specific for the nucleic acid to be detected. On the other hand the present invention also enables a common detection of all nucleic acids which have a certain partial sequence but which differ in other regions (e.g. members of a topological group, e.g. bacteria of one family) either by the probe having isolated and possibly different mismatches to the various nucleic acids that are to be detected as a group but is long enough that a hybridization nevertheless occurs with all members of the group or by selecting hybridization conditions for the binding of the probe which, despite the occurrence of mismatches, allow hybridization with all members of the group or by selecting the probe sequence from a sequence region that is strongly conserved within the group.

The probe P is a molecule which protects the nucleic acid in the region of the partial sequence S against degradation. The probe is also preferably itself resistant to degradation under the selected conditions. Therefore the probes can, on the one hand, be probes with the natural sugar phosphate backbone e.g. oligonucleotides and also with a backbone which differs from the natural sugar phosphate backbone e.g. a peptide backbone or a 2'-allylribose phosphate or a mixture thereof. Preferred probes are described in WO 92/20702. These probes have an increased affinity to complementary nucleic acids compared with the corresponding oligonucleotides of the same base sequence. In particular they can penetrate into DNA—DNA double strands.

The probe P within the sense of the invention has appropriately a defined length and composition and in particular a defined size or/and mass. In particular the mass of the probe P is known in advance.

In a first step a binding product B1 is formed from the nucleic acid to be detected and the probe P. For this the sample containing the nucleic acid to be detected is contacted with the probe P. Probe P is preferably in solution and is combined with a certain amount of sample liquid. The binding product can be double-stranded i.e. in each case one strand of the probe P is bound to one strand of the nucleic acid to be detected or it can be triple-stranded e.g. two strands of the nucleic acid to be detected bind to one strand of the probe or two probes or two parts of a probe bind to one strand of the nucleic acid. The conditions for the binding depend on the type of probe and nucleic acid. In the case of a hybridization the stringency can for example be adjusted by varying the salt concentration, the temperature etc.. The specificity of the binding can also be influenced with these parameters. When peptide nucleic acids (PNA) of WO 92/20702 are used, it is also possible to work with very low salt concentrations (less than 100 $\mu$M). In the simplest case binding of the probe to the nucleic acid is initiated by adding the probe to the sample solution containing the nucleic acid. In this case the probe can be used in a dissolved or solid form, as a single reagent or as a reagent mixture with other reagents that are required or desired for the binding or subsequent steps. Additional reagents can for example be buffers. However, in principle any method of combining the probe P with the solution containing the nucleic acid is possible e.g. by adding the sample to a solution of the probe.

In a subsequent step the sample containing the binding product B1 is subjected to conditions in which the nucleic acid is degraded to produce a binding product B2. An important feature of the invention is that the degradation produces a partial nucleic acid F of a defined length. The degradation may occasionally produce a mixture of partial nucleic acids. This may be the case when the degradation is carried out for a relatively long time. Then products may also form which are several nucleotides and preferably less than 5 nucleotides shorter than the probe P. Consequently the partial nucleic acid F preferably contains a part which is complementary to the partial sequence S even though the fact that the probe P has hybridized and thus a partial nucleic acid F has formed can serve as an indication for the original presence of the partial sequence S. This does not interfere providing the main product which is the basis for the later measurement constitutes more than ca. 50% and preferably more than 70% of the mixture. Of course the sensitivity of the determination is the higher the more main product is present. A person skilled in the art can recognize the main product of the degradation i.e. which partial nucleic acid should be the object of the mass determination by previously recording a mass spectrum and selecting the highest signal. This partial nucleic acid is part of the nucleic acid that was originally bound to the probe P. In this case the partial sequence S is not degraded. Although it is also possible not to completely degrade the nucleic acid down to the partial sequence S, it is preferable to completely degrade the nucleic acid to leave only the bases which bind to the probe P. Degradation of a nucleic acid is preferably understood as a reduction in the length of the nucleic acid especially in the regions outside the partial sequence S e.g. by removing single-stranded regions, by one or several double-stranded cleavages and in particular while maintaining the binding of the probe P to the partial sequence S.

In principle the degradation can be carried out in any manner. However, it is preferably carried out enzymatically. Suitable enzymes have single-strand and/or double-strand-digesting as well as DNA and/or RNA-digesting activities such as nucleases in particular DNases, RNases or restriction endonucleases e.g. DNase I from bovine pancreas (e.g. Lindberg, U., Biochemistry, 1967, 6, 335; Lankowski, M., The Enzymes, 1961, 5, 125; Clark, P. et al., Biochemistry 1974, 13, 5098), exonuclease V from micrococcus luteuas (e.g. Anai, M. et al., J. Biol. Chem. 1970, 245, 767), nuclease S7 from *Staphylococcus aureus* (e.g. Alexander, M. et al., J. Biol. Chem., 1961, 236, 3014; Chsaka, A. et al, J. Biol. Chem., 1964, 239, 3498; Lankowski, M., The Enzymes, 1961, 5, 142), nuclease S1 from *Aspergillus oryzae* (e.g. Ando, T., Biochim. Biophys. Acta, 1966, 114, 158; Vogt, V. M., Eur. Biochem., 1973, 33, 192; Vogt, V. M., Methods Enzymol. 1980, 65, 248) or mung bean nuclease from the shoots of mung beans (e.g. Sung, S. C. et al., J. Biol. Chem. 1962, 237, 506). The enzyme is selected according to the type of nucleic acid to be degraded (ds DNA or/and RNA). The use of enzyme mixtures e.g DNase I and nuclease S1 is also advantageous.

The degradation reaction is preferably carried out until the nucleic acids bound to the probe have a defined constant length. All nucleic acids that are not to be detected that are present in the sample apart from the nucleic acid to be detected should also be preferably degraded as completely as possible. This process depends on the conditions used but is usually completed in less than 2 hours and preferably in less than 30 minutes. The solution then contains the binding product B2 with a defined average mass (depending in particular on the length of the probe P) and possibly excess probe P with a lower but defined mass, low molecular degradation products e.g. mononucleotides which usually have undefined and different low masses and enzymes e.g. DNases with high masses (usually more than 20,000 D). The binding product B2 is now composed of the probe P and the shortened nucleic acid (partial nucleic acid F) which contains the partial sequence S. Hence the binding product B2 has a mass which, with a constant and defined probe mass SM, depends on the length and base composition of the partial sequence F with the mass FM. By selection of the degradation conditions the mass M of the complex can now be used to determine either the length or the base composition. The base composition is also dependent on the sequence of the nucleic acid to be detected within the partial sequence S. If desired the binding products or parts thereof can be also purified after the degradation and before the measurement although the invention is particularly advantageous for measurement in a mixture.

BRIEF DESCRIPTION OF THE DRAWINGS

The possibilities for detecting a nucleic acid which result from the selection of the degradation conditions are shown in FIG. 1 and FIG. 2.

Figure 1:
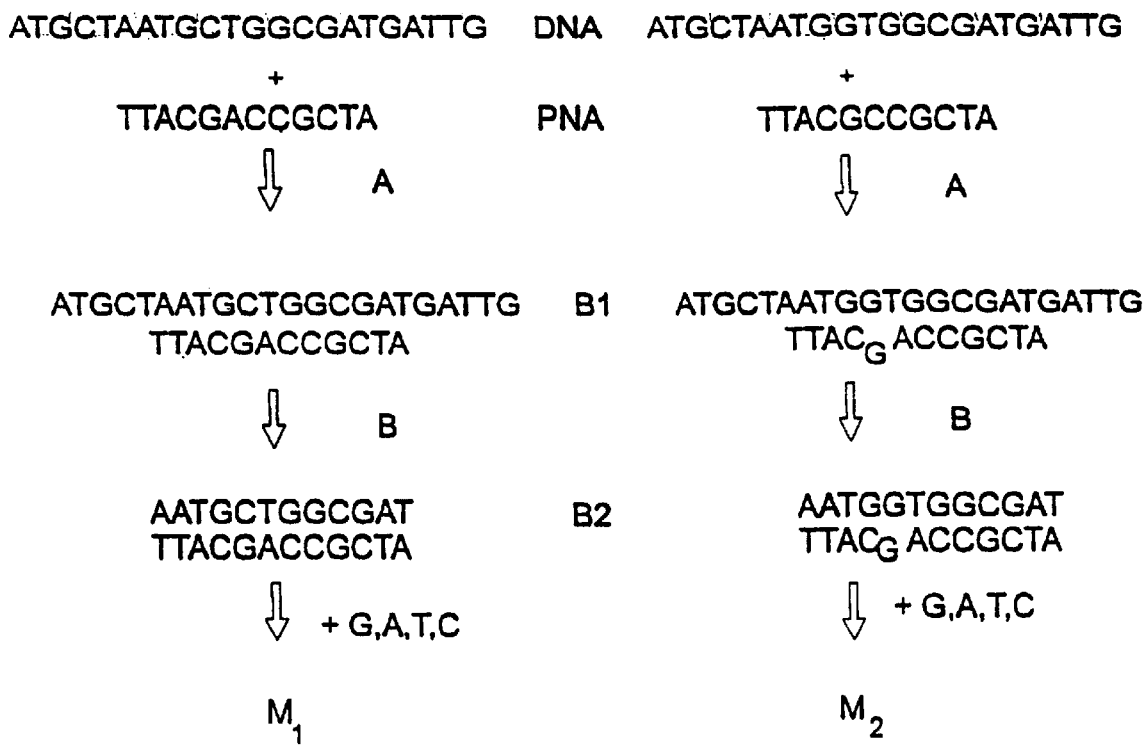
FIG. 1 shows the method according to the invention when two nucleic acids (DNA) are present which differ in one position (position 8) of the base sequence. It shows that binding of the PNA probe to DNA (reaction A) and subsequent digestion of the overhanging single-stranded parts (reaction B) results in two defined complexes each with different molecular weights M1 and M2. The two complexes can be unequivocally classified and identified on the basis of this difference in molecular weight which exactly corresponds to the difference between the bases C and G.

In alternative methods the determination can also be carried out by detecting the mass of part of the binding product B2 and in particular a part with more than 5 bases, preferably of the partial nucleic acid F which is released during ionisation from the binding product B2.

The binding product B2 is detected according to the invention on the basis of its mass. The mass of single- or double-stranded nucleic acid can in principle be determined by mass spectrometry. According to the present state of the art soft ionisation procedures are suitable for recording a mass spectrum of the binding product B2, the partial nucleic acid F or the probe P and the method of atmospheric pressure ionisation (API), in particular electrospray ionisation (ESI, according to Griffith et al., JACS 1995, 117, 831), is particularly suitable. A suitable method is also described in Analytical Chemistry, vol. 68, 3, 527–533 (1996). Only the ionisation procedure that is used is relevant for the detection method described here. Basically all mass analysers that can be coupled with these ionisation procedures can be used to determine the mass of the ions formed in the ionisation e.g. quadrupole mass spectrometers, time-of-flight mass spectrometers, ion traps or sector field instruments. The mass analysers can also be operated in the MS/MS or $MS^\Omega$ mode to improve the selectivity or sensitivity. Matrix-assisted laser desorption ionisation (MADLI) can also be used as an ionisation procedure. The MALDITOF method according to U. Pieles et al., Nucl. Acids Res. 1993, vol. 21, 3191 or Anal. Chem. 1995, 67, 4139–4144) appears to be particularly suitable. The measurement can be carried out with positively-charged ions as well as preferably with negatively-charged ions. In order to measure the sample with negatively-charged ions using ESI, the reaction mixture is for example dissolved in ammonium acetate buffer and this buffer solution is fed into the ionisation system at flow rates between 10 nl/min and 1 ml/min. The ions are formed by atomizing the solution in an electric field whereby this process can be pneumatically assisted by feeding in a gas or thermally assisted. The ions that are formed are focused in the electric field and are transferred via suitable diaphragms or capillaries into the high vacuum region of the mass spectrometer. Ion series of singly or multiply deprotonated molecules are typically formed under these ionisation conditions whose ratios of mass to charge are for example determined with a quadrupole mass analyser. The molecular weight of the components contained in the sample can be calculated from the ion series that are obtained (J. B. Fenn et al., Science 1989, 246, 64–70). The intensities of the ions that are obtained correlate with the concentration of the components in the solution. Adducts such as e.g. sodium or potassium adducts that sometimes occur in the ionisation process can also be used for the evaluation. Positively-charged ions are measured for example in buffer solutions containing acetic acid to produce ionisation series of protonated molecules. The measurement and evaluation is carried out similar to the measurement in the negative mode.

Instruments for recording such mass spectra can for example be obtained from the companies Finnigan MAT, Perkin Elmer Sciex, Bruker, MicroMass and others. The accuracy of the measurement should be ca. 0.01% (ESI) or 0.1% (MALDITOF) deviation from the calculated mass which corresponds to ca. ±1–2 Daltons.

As an alternative to determining the mass of the sample directly in the complete reaction mixture, it is also possible to purify or enrich the sample before the measurement. Filtration processes (ultrafiltration) or chromatographic purification processes are preferably used for this of which the chromatographic processes can be in particular automated and can be used as a direct coupling process with the mass spectrometry. Chromatographic processes are for example reverse phase, ion exchange, gel permeation and affinity chromatography. Electrophoresis and in particular capillary electrophoretic processes are also well suited. The mass of the binding product B2 is a direct or indirect indicator of the nucleic acid to be detected. In the case of the left column in FIG. 1 the expected mass can be determined directly from the probe sequence that was used since the 100% complementarity of the probe to the partial sequence S results in a defined molecular weight. The appearance of a signal for exactly this mass is therefore an indication of the presence of the nucleic acid to be detected. The mass of the partial nucleic acid F detected in other methods is also indicative of the presence of the nucleic acid to be detected.

In the case of the right column of FIG. 1 the deviation $\Delta M$ allows the conclusion that the nucleic acid to be detected differs from the sequence expected in the case of 100% complementarity by a C/G substitution. This can be used to detect precisely this mutation. The mutation C–>G is present if the mass of the signal that is determined differs from the signal which was calculated for 100% complementarity by the difference between the bases G and C. This shows that the method according to the invention can be very advantageously used for the specific determination of individual mutations since the size of the difference between the measured and the expected signal indicates a base substitution and especially one in particular.

Figure 2:
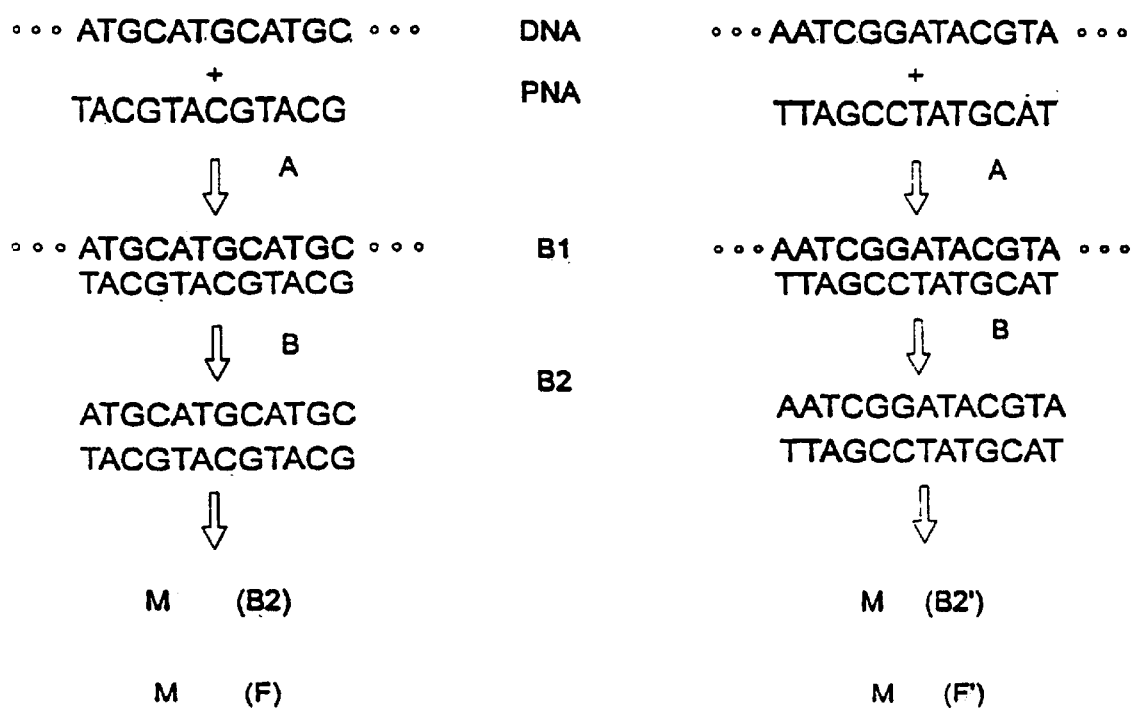
FIG. 2 shows a case in which two different nucleic acids can be determined simultaneously. Each of the two nucleic acid sequences has different partial sequences S. PNA probes (12 mer and 13 mer) of different lengths that are complementary to the respective partial sequence S are hybridized to the corresponding nucleic acids. The binding products B1 and B1' form. After enzymatic degradation of the partial sequences S that are not protected by the probes, one obtains the binding products B2 and B2' with different masses M1 (B2) and M2 (B2'). The reactions shown can be carried out simultaneously in a single test mixture. The presence of the binding product B2 indicates the presence of the nucleic acid to be detected. For this the mass of either the binding product B2 or a part thereof is determined. Parts of B2 that are suitable for a determination are for example the probe P and the partial nucleic acid F. The determination of the partial nucleic acid F is preferred. This can be carried out by for example destroying the binding product B2 to release the partial nucleic acid e.g. by strand separation by treatment with alkali.

However, the method according to the invention can also be used for the simultaneous detection of nucleic acids with different sequences as shown in FIG. 2. In this case two or several probes P1, P2 . . . PN are contacted with the sample instead of one probe P. Each of these probes results in a signal with a predetermined mass when the nucleic acid is present. Since there is almost no limit to the number and selection of possible probes P with different sequences and optionally of different lengths, this method can be used to detect almost any number of different nucleic acids. However, the methods of the prior art require numerous different labels and possibly different detection methods in exactly this case. Therefore the invention also concerns a mixture of probes P1, P2 . . . PN of different masses where these probes are soluble in common solutions containing nucleic acids and where N is a natural number and indicates the number of different probes. The different masses are either achieved by different sequences or by different lengths or by different modifying groups or combinations thereof. The other properties according to the invention of the probes also apply in this case. Thus each of the probes P1, P2 . . . PN is able to form a different binding product B1 with the matching nucleic acid provided it is present in the sample to be examined. The probes are preferably those which do not occur naturally e.g. PNA. The different probes are preferably present in the same constituent amounts or at least in amounts that do not differ greatly in order to use approximately the same conditions for the determination.

The method according to the invention is also particularly suitable for detecting mutations if a probe is used in each case which is 100% complementary to the region of the allele in which the mutation could be located.

The method according to the invention is also particularly suitable for the quantitative detection of nucleic acids if nucleic acids or fragments of a known sequence (standard nucleic acids SN) and matching (e.g. 100% complementary) standard probes SP are added to the reaction mixture and these are subjected to the same treatment as the nucleic acids to be detected. In this case a signal is expected at a predetermined mass and can also be measured. The intensity of the signal is proportional to the concentration. The level of the signal for the (known or defined amounts) standard nucleic acid can now be used to determine the amount of nucleic acid to be detected by comparing or/and forming a ratio between the level of the signal at the mass expected for the nucleic acid to be detected and the level of the signal for the standard nucleic acid.

In addition to a quantitative evaluation, the use of a standard nucleic acid also allows a control for correct test function. If no signal can be measured the test is defective.

In one variant the probe P can also be labelled e.g. by a chemical group which distinguishes a probe with a specific sequence from a probe with the same mass but with another sequence. This also enables a differentiation between nucleic acids with very closely related sequences. Several probes that are labelled differently can also be used for simultaneous tests. The probes can also be provided with groups which facilitate the ionisation e.g. negatively-charged groups for recording a mass spectrum in the negative mode such as carboxyl or sulfonic acid groups or positively-charged groups for the positive mode. These groups are preferably present several times i.e. the probe then has poly- or oligo-anionic or cationic properties. These groups increase the sensitivity of the mass spectrometric determination.

The presence of a partial sequence S can be determined at two levels in the method according to the invention. Firstly the presence of a defined partial nucleic acid F, i.e. its ability to survive the degradation conditions, is already an indication for the presence of the partial sequence S and, on the other hand, the determination of the mass can either be used to confirm the sequence of the partial nucleic acid F or of the partial sequence S or to determine deviations in the sequence.

The method according to the invention can be used successfully in many different ways. It is optionally a homogeneous method i.e. the chemical reactions that are involved take place preferably in one phase, preferably a liquid phase. Such reactions occur under conditions that are easier to control and proceed more rapidly. Moreover the method according to the invention can be more rapid than previously available methods. It can also be more sensitive than conventional methods and may even be able to circumvent an amplification of the nucleic acids to be detected. It is possible to avoid the use of labelled probes. Since the presence of a quite particular mass is used for the test result, the apparatus can be designed to give a high resolution exactly in the required mass range. The other products which are formed during the process or that are added (e.g. single-stranded fragments or probes) have a significantly different mass from the binding product B2 or from the partial nucleic acid F.

The method can also be automated. Furthermore the method according to the invention is excellently suitable for the simultaneous determination of several nucleic acids with different sequences or different sequences of one nucleic acid. In this case a combination of several PNAs is used which are complementary to these sequences.

In a particularly preferred embodiment the procedure is as follows:

In a first step the nucleic acid to be detected is optionally released from the cells by lysis. The nucleic acid is subsequently immobilized on a solid surface e.g. a glass-like surface and the remaining sample liquid is removed. Then the nucleic acid is detached from the surface and a partial sequence is amplified by PCR.

In a next step a PNA probe P with a complementary sequence to a binding product B1 is hybridized to a partial sequence S of an amplified nucleic acid. In a subsequent step the binding product B1 is digested with a nuclease mixture in an optimal enzyme buffer and at an optimal temperature for the enzymes that are used to form the binding product B2 which is now composed of the partial nucleic acid F with the partial sequence S and the PNA probe P. B2 is freed of the other reaction components by means of ion exchange chromatography and subsequently the fraction containing B2 is fed into the mass spectrometric system. The mass of the binding product B2 or of the partial nucleic acid F is determined.

The invention is further elucidated by the following example:

EXAMPLE 2.7 nmol (5 μl in water) of an oligonucleotide with the sequence 5'-TAT TAG GCC ATC GTC TTC ATG GTC CAG AAC ACC AAC AGG AAG ACC-3' (SEQ ID NO.1) and 2.7 nmol (5 μl in water) PNA with the sequence $H_2N$-AAG TAC CAG GTC TTG-H are added by pipette, then 10 μl 2×assay buffer (60 mM Na acetate, 100 mM NaCl, 2 mM Zn acetate, 0.002% Triton X-100, pH 4.6) is added. The sample is heated for 3 min to 95° C. and is then cooled to 37° C. Subsequently 1 U mung bean nuclease I (Boehringer Mannheim) is added and the sample is incubated for 10 min at 37° C. The enzyme reaction is terminated by addition of 1 mM EDTA (25 μl). Afterwards the solution is diluted with water to 0.5 ml and desalted by means of NAP-5 (Pharmacia).

A method according to Wilm et al., Analytical Chemistry 68 (1996), 527–533 (Parent Ion Scans of Unseparated Peptide Mixtures) is used for the mass spectrometric analysis. Mass spectrometer API III triple quadrupole with collision cell (Perkin-Elmer Sciex Instrument) with nonoelectrospray ion source; polarity negative mode, spray potential −750 V, scan range 350–1400 Da, step width 0.2 Da, dwell time 1 ms; 11 scans added up, precursor ion scan mode for ion m/z 79, collision gas argon, collision energy 35 eV/charge.

Figure 3:
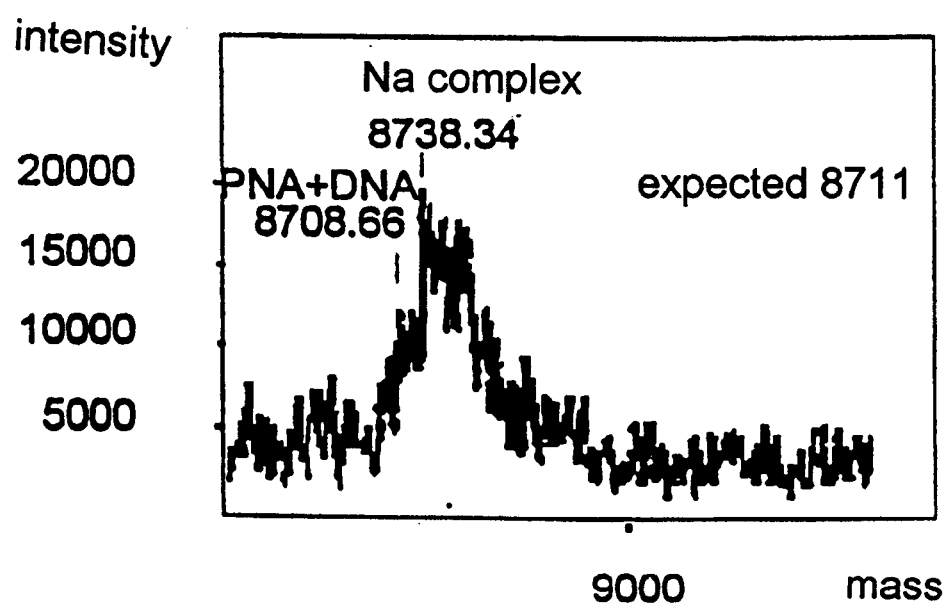
FIG. 3 shows a typical spectrum for a PNA-DNA duplex.

A typical spectrum for the PNA-DNA duplex is shown in FIG. 3. After deconvolution of the raw data, a molecular weight of 8709 Da (theoretically expected 8711 Da) is obtained for the duplex.

What is claimed is:

1. A method for qualitatively or quantitatively detecting a sample nucleic acid containing a sequence S, the method comprising:

binding a probe P, which is comprised of peptide nucleic acid, to the sequence S contained in the sample nucleic acid to produce a binding product B1;

degrading the sample nucleic acid to produce a binding product B2 comprising the probe P and a degraded nucleic acid F comprising the sequence S, wherein the degraded nucleic acid F is shorter than the sample nucleic acid; and qualitatively or quantitatively detecting the binding product B2 using mass spectrometry, thereby detecting the sample nucleic acid.

2. The method of claim 1, wherein the sample nucleic acid is double-stranded.

3. The method of claim 1, wherein the sample nucleic acid is single-stranded.

4. The method of claim 1, wherein the sequence S is larger than 5 nucleotides.

5. The method of claim 1, wherein the sequence S is between 6 and 100 nucleotides.

6. The method of claim 1, wherein the sequence S is between 10 and 30 nucleotides.

7. The method of claim 1, wherein the sequence S indicates an infection by an organism, a genetic disease, or a predisposition to a genetic disease.

8. The method of claim 7, wherein the sequence S indicates an infection by hepatitis C virus.

9. The method of claim 1, wherein the degraded nucleic acid F consists of the sequence S.

10. The method of claim 1, wherein said degrading step is carried out enzymatically.

11. The method of claim 10, wherein said degrading step is carried out for less than 2 hours.

12. The method of claim 10, wherein said degrading step is carried out for less than 30 minutes.

13. The method of claim 1, wherein after said degrading step, the binding product B2 is purified.

14. The method of claim 1, wherein during said degrading step, the probe P protects the sequence S from degradation.

15. The method of claim 10, wherein said degrading step is carried out using S1 nuclease, DNase 1, Micrococcus nuclease or mung bean nuclease.

16. The method of claim 1, wherein before said binding step, the sample nucleic acid is purified.

17. A method for qualitatively or quantitatively detecting a plurality of sample nucleic acids, each containing a different sequence S, the method comprising:

binding each of a plurality of different probes P, each of which is comprised of peptide nucleic acid, to a corresponding different sequence S contained in the sample nucleic acids to produce a plurality of binding products B1;

degrading the plurality of sample nucleic acids to produce a plurality of binding products B2, each comprising one of the plurality of probes P and one of a plurality of degraded nucleic acids F, each of which comprises one of the sequences S, wherein the degraded nucleic acids F are shorter than the sample nucleic acids; and qualitatively or quantitatively detecting the binding products B2 using mass spectrometry, thereby detecting the sample nucleic acids.

\* \* \* \* \*